(12) United States Patent
Cheng

(10) Patent No.: US 11,098,373 B2
(45) Date of Patent: *Aug. 24, 2021

(54) DETECTION OF GENE FUSIONS BY INTRAGENIC DIFFERENTIAL EXPRESSION (IDE) USING AVERAGE CYCLE THRESHOLDS

(71) Applicant: Quest Diagnostics Investments LLC, Secaucus, NJ (US)

(72) Inventor: Shih-Min Cheng, Irvine, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/683,893

(22) Filed: Nov. 14, 2019

(65) Prior Publication Data

US 2020/0157641 A1 May 21, 2020

Related U.S. Application Data

(63) Continuation of application No. 15/916,828, filed on Mar. 9, 2018, now Pat. No. 10,487,367, which is a continuation of application No. 14/667,205, filed on Mar. 24, 2015, now Pat. No. 9,914,973.

(60) Provisional application No. 61/969,897, filed on Mar. 25, 2014.

(51) Int. Cl.
*C12P 19/34* (2006.01)
*C12Q 1/6886* (2018.01)
*C12Q 1/6858* (2018.01)

(52) U.S. Cl.
CPC ......... *C12Q 1/6886* (2013.01); *C12Q 1/6858* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 6,174,674 | B1 | 1/2001 | Morris et al. |
| 8,426,133 | B2 | 4/2013 | Sanders et al. |
| 8,815,516 | B2 | 8/2014 | Sanders et al. |
| 9,187,788 | B2 | 11/2015 | Sanders et al. |
| 9,546,404 | B2 | 1/2017 | Sanders et al. |
| 2003/0096255 | A1 | 5/2003 | Felix et al. |
| 2010/0304390 | A1 | 12/2010 | Sanders et al. |
| 2012/0202214 | A1 | 8/2012 | Omi et al. |

FOREIGN PATENT DOCUMENTS

| CN | 1854313 A | 11/2006 |
| CN | 101250584 A | 8/2008 |
| CN | 101974623 A | 2/2011 |
| WO | WO 2013/119950 A2 | 8/2013 |

OTHER PUBLICATIONS

Rychlik et al., Nucleic Acids Research 17(21), 8543-8551 (1989). (Year: 1989).*
Takeuchi et al., "RET, ROS1, and ALK fusions in lung cancer," Nature Medicine, vol. 18, No. 3, pp. 378-381, Feb. 12, 2012.
International Search Report issued in application No. PCT/US2015/022230 dated Jul. 1, 2015.
Office Action dated Jul. 2, 2018, in Chinese Application No. 201580027373.0, with machine English translation.
European Search Report dated Apr. 9, 2021 in EP 20205138.9.
Lira et al., "A Single-Tube Multiplexed Assay for Detecting ALK, ROS1, and RET Fusions in Lung Cancer," The Journal of Molecular Diagnostics, Mar. 2014, 16(2):229-243.
Sanders et al., "Exon scanning by reverse transcriptase-polymerase chain reaction for detection of known and novel EML4-ALKK fusion variants in non-small cell lung cancer," Cancer Genetics, 2011 (Aug. 19, 2010), 204(1):45-52.
Schulten et all., "Mutational Screening of RET, HRAS, KRAS, NRAS, BRAF, AKT1, and CTNNB1 in Medullary Thyroid Carcinoma," Anticancer Research, 2011, 31(12):4179-4183.

* cited by examiner

*Primary Examiner* — Kenneth R Horlick
(74) *Attorney, Agent, or Firm* — Foley & Lardner LLP

(57) ABSTRACT

Described herein are methods and kits for detecting the presence or absence of gene dysregulations such as those arising from gene fusions and/or chromosomal abnormalities, e.g. translocations, insertions, inversions and deletions. The methods, compositions and kits are useful for detecting mutations that cause the differential expression of a 5' portion of a target gene relative to the 3' region of the target gene. The average expression of the 5' portion of the target gene is compared with the average expression of the 3' portion of the target gene to determine an intragenic differential expression (IDE). The IDE can then be used to determine if a dysregulation or a particular disease (or susceptibility to a disease) is present or absent in a subject or sample.

29 Claims, 1 Drawing Sheet
Specification includes a Sequence Listing.

(1) In the presence of fusion transcripts
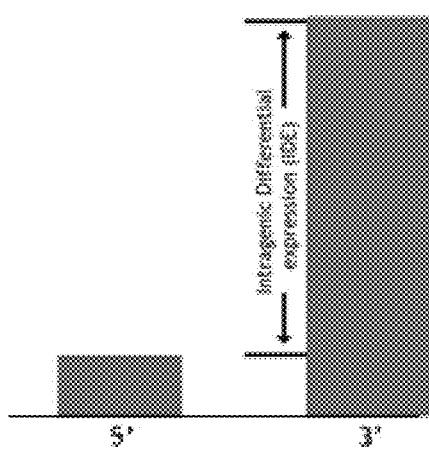
Average expression level
of each gene region
(3' region and 5' region)
(2) In the absence of fusion transcripts
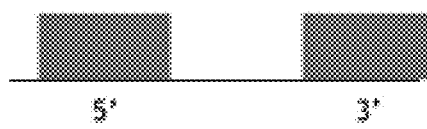
Average expression level
of each gene region
(3' region and 5' region)

DETECTION OF GENE FUSIONS BY INTRAGENIC DIFFERENTIAL EXPRESSION (IDE) USING AVERAGE CYCLE THRESHOLDS

CROSS REFERENCE TO RELATED APPLICATIONS

The present application is a Continuation of U.S. patent application Ser. No. 15/916,828, filed Mar. 9, 2018, now U.S. Pat. No. 10,487,367, which is a Continuation of U.S. patent application Ser. No. 14/667,205 filed Mar. 24, 2015, now U.S. Pat. No. 9,914,973, which claims priority to U.S. Provisional Patent Application No. 61/969,897, filed Mar. 25, 2014, which are incorporated by reference herein in their entirety.

SEQUENCE LISTING

The instant application contains a Sequence Listing which has been submitted electronically via EFS-WEB in ASCII format and is hereby incorporated by reference in its entirety. Said ASCII copy, created on Nov. 12, 2019, is named seqlisting.txt and is 15,303 bytes.

FIELD OF THE INVENTION

The present technology relates generally to detection of gene dysregulations such as those arising from gene translocations and/or fusions, which may be associated with various diseases. In a particular aspect, the present technology relates to the detection of gene dysregulations using quantitative real time-PCR.

BACKGROUND

The following description is provided to assist the understanding of the reader. None of the information provided or references cited is admitted to be prior art to the present invention.

Variations in chromosome structure involve changes in parts of chromosomes rather than changes in the number of chromosomes or sets of chromosomes in the genome. There are four common types of mutations: deletions and duplications (both of which involve a change in the amount of DNA on a chromosome), inversions (which involve a change in the arrangement of a chromosomal segment), and translocations (which involve a rearrangement of portions in nonhomologous chromosomes).

Reciprocal and Robertsonian translocations are the most frequently occurring types of translocations. Reciprocal translocations usually involve a two-way exchange between different chromosomes. The chromosomes break apart and segments below the break points swap positions. If the event is balanced, no net gain or loss of genetic material results and the individual is usually phenotypically unaffected if no genes are disrupted.

Robertsonian translocations occur when two chromosomes fuse at the centers and essentially combine into one. Most of the genetic material remains from both chromosomes. As in balanced reciprocal translocations, the carrier may be normal, but produce genetically unbalanced gametes. Most progeny originating from unbalanced gametes do not survive and a miscarriage occurs during early pregnancy. If the carrier is fertile and progeny survive, various defects could occur. One Robertsonian translocation results in the fusion of chromosomes 14 and 21. Resulting progeny may inherit three copies of chromosome 21 which causes Down's syndrome.

A gene fusion may result when a translocation joins portions of two otherwise separated genes. Such an occurrence is common in some cancers such as non-small cell lung cancer (NSCLC).

Anaplastic lymphoma kinase (ALK) is a receptor tyrosine kinase that is frequently involved in gene fusions in hematological disorders and has at least 4 reported fusion partners in NSCLC: EML4, KLC1, KIFSB, and TFG (3-5). The gene fusion products (found in 3-7% NSCLC) lead to constitutive ALK kinase activation and serve as oncogenic drivers with transforming ability. The development of tyrosine kinase inhibitors (TKIs) targeting the EML4-ALK fusion products has been successful and crizotinib was approved by FDA in 2011 to treat NSCLC patients with ALK translocations, along with the ALK fluorescent in situ hybridization (FISH) test as companion diagnostic. (6).

ROS1, like ALK, is a receptor tyrosine kinase. Approximately 1.7% of NSCLC harbor ROS1 translocation and ROS1 has at least 7 fusion partners: FIG, GOPC, TPM3, SDC4, SLC34A2, CD74 and EXR (7-9). Similar to ALK, ROS1 fusion products lead to constitutive kinase activity and are sensitive to TKIs. Although there are currently no specific ROS1 inhibitors in clinical trials, data suggest that NSCLC patients with ROS1 translocations could benefit from targeted therapy using crizotinib (10).

RET (rearranged during transfection) is another receptor tyrosine kinase and is known for its association with papillary thyroid cancer through chromosome rearrangements (RET/PTC). About 1.9% of NSCLC carry RET translocations with at least 2 fusion partners: KIFSB and CCDC6 (7, 9). Additionally, RET translocations in NSCLC are potential targets for TKIs like vandetanib, which is approved for the treatment of thyroid cancer (11).

Non-small cell lung cancer (NSCLC) accounts for about 80% of all lung cancer cases. In the last decade, the characterization of genetic alterations in NSCLC has led to the development of novel therapeutic treatments, like gefitinib and erlotinib for NSCLC patients with EGFR mutations (2). In general, EGFR mutation, KRAS mutation, ALK, ROS1, and RET translocations are mutually exclusive in NSCLC patients. Improved methods for detecting translocations such as, for example, ALK, ROS1, and RET translocations in subjects such as, for example, NSCLC patients would be useful for identifying patients who would benefit from targeted therapeutic treatments with TKIs like crizotinib and vandetanib. A panel and/or kit to detect such translocations also would be useful.

SUMMARY OF THE INVENTION

Described herein are methods, compositions, and kits for detecting gene dysregulations such as those arising from gene fusions and chromosomal translocations. The methods, compositions and kits are useful for detecting mutations that cause the differential expression of a 5' region of a target gene relative to the 3' region of the target gene. A sensitive, accurate, and cost effective assay to detect ALK, ROS1, and RET translocations in NSCLC patients is also disclosed. A method for diagnosing cancer is also described.

In one aspect, the present disclosure provides a method for detecting the presence or absence of a dysregulation in a target gene in a test sample. In one embodiment, the method includes: (a) amplifying portions of a 5' region of a transcript of the target gene or a cDNA derived therefrom, if present in a test sample, with two or more different 5' target primer pairs that are directed to the portions of the 5' region of the target gene; (b) amplifying portions of a 3' region of a transcript of the target gene or a cDNA derived therefrom, if present in the test sample, with two or more different 3' target primer pairs that are directed to the portions of 3' region of the target gene; (c) detecting the amplification products produced by the two or more 5' target primer pairs and the two or more 3' target primer pairs; (d) determining the average cycle threshold (Ct) among the two or more 5' target primer pairs and the average Ct among the two or more 3' target primer pairs, (e) calculating an IDE Score as the difference between the average cycle threshold among the 5' target primer pairs and the average cycle threshold among the 3' target primer pairs, and (f) identifying the test sample as (i) having a target gene dysregulation if the IDE Score is significantly different than a cutoff value and the difference indicates the presence of a target gene dysregulation, or (ii) not having a target gene dysregulation if the IDE Score in the test sample does not differ significantly from the cutoff value.

In another aspect, the present disclosure provides a method for diagnosing the presence or absence of cancer or a susceptibility to cancer in a subject. In one embodiment, the method includes: (a) obtaining a test sample that comprises nucleic acid from the subject; (b) amplifying portions of a 5' region of a transcript of a target gene or a cDNA derived therefrom, if present in the test sample, with two or more different 5' target primer pairs that are directed to the portions of the 5' region of the target gene; (c) amplifying portions of a 3' region of a transcript of the target gene or a cDNA derived therefrom, if present in the test sample, with two or more different 3' target primer pairs that are directed to the portions of the 3' region of the target gene; (d) detecting the amplification products produced by the two or more 5' target primer pairs and the two or more 3' target primer pairs; (e) determining the average cycle threshold (Ct) among the two or more 5' target primer pairs and the average Ct among the two or more 3' target primer pairs; (f) calculating an IDE Score as the difference between the average cycle threshold among the 5' target primer pairs and the average cycle threshold among the 3' target primer pairs, and (g) diagnosing the subject as (i) having cancer or a susceptibility to cancer when the IDE Score is significantly different than a cutoff value and the difference indicates the presence of cancer or a susceptibility to cancer, or (ii) not having cancer or a susceptibility to cancer resulting from dysregulation of the target gene if the IDE Score in the test sample does not differ significantly from the cutoff value.

In some embodiments, the subject is a human and the cancer is non-small cell lung cancer. Exemplary target genes that may be assayed for translocation to detect the presence of absence of NSCLC are, ROS1, RET and ALK. In some embodiments, these three genes constitute a NSCLC panel and are all analyzed using the disclosed methods.

A sample may be a biological sample or another sample containing nucleic acids such as, for example, mRNA or cDNA. Amplification may be performed using real-time PCR and detection of amplification products may be performed using detectably labeled probe(s), such as an oligonucleotide probe that comprises a detectable label.

In some embodiments of the methods disclosed herein, the expression level of the 5' region of a target gene is determined by amplification using two, three, four, five or six different primer pairs directed to various portions of the 5' region of the target gene. Similarly, two, three, four, five or six different primer pairs directed to various portions of the 3' region of the target gene may be used to determine the expression level of the 3' region of the target gene. The amounts of amplification products each may be normalized to the amount of an endogenous control gene transcript ("Control") such as, for example, ABL.

In some embodiments, the expression level or relative amount of transcript can be determined using real-time PCR and comparing the threshold cycle (Ct) for each amplicon. The average Ct values for each of the 3' ($avgCt_{3'}$) and 5' ($avgCt_{5'}$) regions of a target gene are used to calculate an IDE Score, which may be calculated as $IDE=(avgCt_{5'}-avgCt_{3'})$, or $IDE=(avgCt_{5'})/(Ct_{control})-(avgCt_{3'})/(Ct_{control})$, or $IDE=[Ln((avgCt_{5'})/Ct_{control})]-[Ln((avgCt_{3'})/Ct_{control})]$. In some embodiments, the Ct values are normalized to a reference sample.

Biological samples such as, for example, whole blood, isolated blood cells, plasma, serum, and urine may be analyzed using the disclosed methods.

BRIEF DESCRIPTION OF THE DRAWINGS

FIG. 1 is a diagram illustrating the determination of intragenic differential expression (IDE) based on average expression levels of 5' regions and 3' regions of a gene to detect the presence or absence of a fusion transcript. Part (1) shows the difference in expression levels (IDE) between the 5' region and 3' region, indicating the presence of a fusion transcript. Part (2) shows equal levels of expression of the 5' region and 3' region, indicating no fusion transcript present.

DETAILED DESCRIPTION

Described herein are methods, reagents and kits for detecting gene dysregulations such as those arising as a result of gene fusions or chromosome translocations, in a sample, where the dysregulation leads to differential expression or quantities of particular portions of target genes. Translocations are mutations whose effect is to juxtapose previously separate pieces of DNA, potentially bringing together separate genes to form functionally distinct fusion genes (e.g., ROS1-FIG, ROS1-TPM3 and ROS1-SLC34A2).

To facilitate an understanding of the present invention, a number of terms and phrases are defined below.

As used herein, unless otherwise stated, the singular forms "a," "an," and "the" include plural reference. Thus, for example, a reference to "an oligonucleotide" includes a plurality of oligonucleotide molecules, a reference to label is a reference to one or more labels, a reference to probe is a reference to one or more probes, and a reference to "a nucleic acid" is a reference to one or more polynucleotides.

As used herein, unless indicated otherwise, when referring to a numerical value, the term "about" means plus or minus 10% of the enumerated value.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplification product." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, Saiki, "Amplification of Genomic DNA" in PCR Protocols, Innis et al., Eds., Academic Press, San Diego, Calif. 1990, pp. 13-20; Wharam et al., Nucleic Acids Res., 29(11):E54-E54, 2001; Hafner et al., Biotechniques, 30(4):852-56, 858, 860, 2001: Zhong et al., Biotechniques, 30(4):852-6, 858, 860, 2001.

As used herein, the term "detecting" refers to observing a signal from a detectable label to indicate the presence of a target nucleic acid in the sample. The term detecting does not require the method to provide 100% sensitivity and/or 100% specificity. As is well known, "sensitivity" is the probability that a test is positive, given that the subject has a target nucleic acid sequence, while "specificity" is the probability that a test is negative, given that the subject does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

The terms "complement," "complementary" or "complementarity" as used herein with reference to polynucleotides (i.e., a sequence of nucleotides such as an oligonucleotide or a genomic nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association". For example, for the sequence 5'-A-G-T-3' is complementary to the sequence 3'-T-C-A-S'. Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Complementarity may be "partial" in which only some of the nucleic acids' bases are matched according to the base pairing rules. Or, there may be "complete," "total," or "full" complementarity between the nucleic acids.

The term "detectable label" as used herein refers to a molecule or a compound or a group of molecules or a group of compounds associated with a probe and is used to identify the probe hybridized to a genomic nucleic acid or reference nucleic acid. In some cases, the detectable label may be detected directly. In other cases, the detectable label may be a part of a binding pair, which can then be subsequently detected. Signals from the detectable label may be detected by various means and will depend on the nature of the detectable label. Examples of means to detect detectable label include but are not limited to spectroscopic, photochemical, biochemical, immunochemical, electromagnetic, radiochemical, or chemical means, such as fluorescence, chemifluoresence, or chemiluminescence, or any other appropriate means.

A "fragment" in the context of a gene fragment or a chromosome fragment refers to a sequence of nucleotide residues which are at least about 10 nucleotides, at least about 20 nucleotides, at least about 25 nucleotides, at least about 30 nucleotides, at least about 40 nucleotides, at least about 50 nucleotides, at least about 100 nucleotides, at least about 250 nucleotides, at least about 500 nucleotides, at least about 1,000 nucleotides, at least about 2,000 nucleotides, at least about 5,000 nucleotides, at least about 10,000 nucleotides, at least about 20,000 nucleotides, at least about 50,000 nucleotides, at least about 100,000 nucleotides, at least about 500,000 nucleotides, at least about 1,000,000 nucleotides or more.

The term "genetic abnormality" or "chromosomal abnormality" as used herein refers to a deviation of the nucleic acid sequence from a wild-type or normal genetic sequence. A genetic abnormality may reflect a difference between the full genetic complement of an organism, or any portion thereof, as compared to a normal full genetic complement of all chromosomes in that organism. For example, a genetic abnormality may include a change in chromosomes or a portion thereof (e.g., deletions, duplications, amplifications); or a change in chromosomal structure (e.g., translocations, point mutations). Genetic abnormality may be hereditary, i.e., passed from generation to generation or non-hereditary. Genetic abnormalities may be present in some cells of an organism or in all cells of that organism.

The term "endogenous control gene" as used herein refers to genes that are generally always expressed and thought to be involved in routine cellular metabolism. Endogenous control genes are well known and include such genes as ABL, glyceraldehyde-3-phosphate dehydrogenase (G3PDH or GAPDH), albumin, actins, tubulins, cyclophilin, hypoxanthine phosphoribosyltransferase (HRPT), L32. 28S, and 18S rRNAs. Detection of endogenous control genes in a diagnostic assay may serve as a positive control for the assay.

The terms "identity" and "identical" refer to a degree of identity between sequences. There may be partial identity or complete identity. A partially identical sequence is one that is less than 100% identical to another sequence. Partially identical sequences may have an overall identity of at least 70% or at least 75%, at least 80% or at least 85%, or at least 90% or at least 95%.

As used herein, the terms "isolated", "purified" or "substantially purified" refer to molecules, such as nucleic acid, that are removed from their natural environment, isolated or separated, and are at least 60% free, preferably 75% free, and most preferably 90% free from other components with which they are naturally associated. An isolated molecule is therefore a substantially purified molecule.

The term "multiplex PCR" as used herein refers to an assay that provides for simultaneous amplification and detection of two or more products within the same reaction vessel. Each product is primed using a distinct primer pair. A multiplex reaction may further include specific probes for each product that are detectably labeled with different detectable moieties.

As used herein, the term "oligonucleotide" refers to a short polymer composed of deoxyribonucleotides, ribonucleotides or any combination thereof. Oligonucleotides are generally between about 10, 11, 12, 13, 14, 15, 20, 25, or 30 to about 150 nucleotides (nt) in length, more preferably about 10, 11, 12, 13, 14, 15, 20, 25, or 30 to about 70 nt, and most preferably between about 18 to about 26 nt in length.

An oligonucleotide (e.g., a probe or a primer) that is specific for a target nucleic acid will "hybridize" to the target nucleic acid under stringent conditions. As used herein, "hybridization" or "hybridizing" refers to the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the $T_m$, of the formed hybrid.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art occur under stringent conditions. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$ and conditions for nucleic acid hybridization are known in the art. "Stringent hybridization conditions" as referenced herein designate 50% formamide, 1 M NaCl, 1% SDS at 37° C. Hybridization procedures are well known in the art and are described in e.g. Ausubel et al, Current Protocols in Molecular Biology, John Wiley & Sons Inc., 1994.

As used herein, a "primer" for amplification is an oligonucleotide that is complementary to a target nucleotide sequence and leads to addition of nucleotides to the 3' end of the primer in the presence of a DNA or RNA polymerase. The 3' nucleotide of the primer should generally be identical to the target nucleic acid sequence at a corresponding nucleotide position for optimal expression and amplification. The term "primer" as used herein includes all forms of primers that may be synthesized including peptide nucleic acid primers, locked nucleic acid primers, phosphorothioate modified primers, labeled primers, and the like. Upstream and downstream PCR primers specific for particular sequences or sequence regions can be designed using available computer programs and/or by applying general rules of primer design known in the art. In some embodiments, the primers of a primer pair are each 18-30 base pairs in length with similar melting temperatures (within 5° C. of each other) and with melting temperatures between 65° and 75° C. In some embodiments, a primer has a GC content between 40 and 60%, and the 3' of each primer ends in C or G to promote binding. When designing primers, regions of secondary structure typically are avoided, and sequences with a balanced distribution of GC-rich and AT-rich domains are preferred. Runs of 4 or more of one base, or dinucleotide repeats (for example, ACCCC or ATATATAT) also typically are avoided.

As used herein, a "forward primer" is a primer that is complementary to the anti-sense strand of dsDNA. A "reverse primer" is complementary to the sense-strand of dsDNA. An "exogenous primer" refers specifically to an oligonucleotide that is added to an amplification reaction vessel containing the sample nucleic acid to be amplified from outside the vessel and is not produced from amplification in the reaction vessel. A primer that is "associated with" a fluorophore or other label is physically connected to the label through some means. An example is a primer-probe. As used herein, a "primer-probe" is a type of primer.

Primers are typically from at least 10, 15, 18, or 30 nucleotides in length up to about 100, 110, 125, or 200 nucleotides in length, preferably from at least 15 up to about 60 nucleotides in length, and most preferably from at least 25 up to about 40 nucleotides in length. In some embodiments, primers and/or probes are 15 to 35 nucleotides in length. There is no standard length for optimal hybridization or polymerase chain reaction amplification. An optimal length for a particular primer application may be readily determined in the manner described in H. Erlich, PCR Technology, Principles and Application for DNA Amplification, (1989).

A "primer pair" is a pair of primers that are both directed to target nucleic acid sequence. A primer pair that is directed to a particular gene or sequence contains a forward primer and a reverse primer, each of which hybridizes under stringent condition to a different strand (sense or antisense) of the nucleic acid sequence. The forward primer is complementary to the anti-sense strand of the dsDNA and the reverse primer is complementary to the sense-strand. One primer of a primer pair may be a primer-probe (i.e., a bi-functional molecule that contains a PCR primer element covalently linked by a polymerase-blocking group to a probe element and, in addition, may contain a fluorophore that interacts with a quencher). A primer pair that specifically hybridizes under stringent conditions to a target gene may flank all or a portion of the gene (that is relatively complementary to the primer sequence). As a result, the entire gene may be amplified or a segment of the gene may be amplified, depending on the position in or around the gene where the primers hybridize. Two or more primer pairs are different if at least one primer sequence from one primer pair is not identical to either primer sequence of the other primer pair. Thus, two primer pairs may be different even if they share one identical primer. In some embodiments. In some embodiments, different primer pairs do not share any common primer sequences.

As used herein, the term "primer-probe detection system" refers to a method for real-time PCR. This method utilizes a bi-functional molecule (referred to herein as a primer-probe), which contains a PCR primer element covalently linked by a polymerase-blocking group to a probe element. Additionally, each primer-probe molecule contains a fluorophore that interacts with a quencher to reduce the background fluorescence. Primer-probes, as used herein, may comprise a 3' primer with a 5' extended probe tail comprising a hairpin structure which possesses a fluorophore/quencher pair. During PCR, the polymerase is blocked from extending into the probe tail by the inclusion of hexethlyene glycol (HEG). During the first round of amplification the 3' target-specific primer anneals to the target nucleic acid and is extended such that the primer-probe is now incorporated into the newly synthesized strand, which possesses a newly synthesized target region for the 5' probe. During the next round of denaturation and annealing, the probe region of the primer-probe hairpin loop will hybridize to the target, thus separating the fluorophore and quencher and creating a measurable signal. Such primer-probes are described in Whitcombe et al., Nature Biotech 17: 804-807 (1999). SCORPION primers are exemplary primer-probes.

As used herein "TaqMan® PCR detection system" refers to a method for real-time PCR. In this method, a TaqMan® probe which hybridizes to the nucleic acid segment amplified is included in the amplification master mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art (e.g., BLAST). As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

The terms "target nucleic acid," "target gene" and "target sequence" are used interchangeably herein and refer to nucleic acid sequence which is intended to be identified. Target nucleic acids may include 5' or 3' regions of a target gene or transcript or any other sequence of interest. Target nucleic acids may represent alternative sequences or alleles of a particular gene. Target nucleic acids can be double stranded or single stranded, or partially double stranded, or partially single stranded or a hairpin molecule, Target nucleic acids can be about 1-5 bases, about 10 bases, about 20 bases, about 50 bases, about 100 bases, about 500 bases, about 1,000 bases, about 2,000 bases, 2,500 bases, about 3,000 bases, about 3,000 bases, about 4,000 bases, about 5,000 bases, about 7,500 bases, about 10,000 bases, about 20,000 bases, about 30,000 bases, about 40,000 bases, about 50,000 bases, about 75,000 bases, about 100,000 bases, about 1,000,000 bases or more.

The term "transcript," when referring to a target nucleic acid, refers to any nucleic acid that is representative of the genomic nucleic acid of a cell including, for example, RNA in any form (e.g., mRNA, pre-mRNA, and snRNA) and synthetic representations of such as cDNA.

The term "test sample" as used herein refers to a sample, which contains nucleic acid or is suspected of containing nucleic acid. In some embodiments, the nucleic acids in the test sample are for use in accordance with the methods disclosed herein. In some embodiments, a test sample is a biological sample obtained from a subject. In some embodiments, a test sample is extracted nucleic acids from a biological sample. In some embodiments a test sample is cDNA that was reverse transcribed from mRNA from a biological sample.

The term "biological sample" as used herein refers to a sample obtained from a subject, which contains target nucleic acids or is used as a source of target nucleic acids for the methods of the invention. A biological sample may include clinical samples (i.e., obtained directly from a patient) or isolated nucleic acids and may be cellular or acellular fluids and/or tissue (e.g., biopsy) samples. In some embodiments, a sample is obtained from a tissue or bodily fluid collected from a subject. Sample sources include, but are not limited to, sputum (processed or unprocessed), bronchial alveolar lavage (BAL), bronchial wash (BW), whole blood or isolated blood cells of any type (e.g., lymphocytes), bodily fluids, cerebrospinal fluid (CSF), urine, plasma, serum, or tissue (e.g., biopsy material). The term "patient sample" as used herein refers to a sample obtained from a human seeking diagnosis and/or treatment of a disease. In the case where the subject is a fetus, the patient sample can be from the subject (i.e., fetus), amniotic fluid, or maternal (e.g. the mother's blood).

As used herein, the term "subject" refers to a mammal, such as a human, but can also be another animal such as a domestic animal (e.g., a dog, cat, or the like), a farm animal a cow, a sheep, a pig, a horse, or the like) or a laboratory animal (e.g., a monkey, a rat, a mouse, a rabbit, a guinea pig, or the like). The term "patient" refers to a "subject" who is, or is suspected to be, afflicted with disease related to a chromosomal abnormality.

A chromosome "translocation" is the interchange of parts between nonhomologous chromosomes. It is generally detected through cytogenetics or a karyotyping of affected cells. There are two main types, reciprocal, in which all of the chromosomal material is retained and Robertsonian, in which some of the chromosomal material is lost. Further, translocations can be balanced (in an even exchange of material with no genetic information extra or missing) or unbalanced (where the exchange of chromosome material is unequal resulting in extra or missing genes).

A reciprocal translocation between chromosomes 9 and 22 resulting in a cytogenetically distinct acrocentric chromosome termed the Philadelphia chromosome. This translocation fuses the BCR gene locus of chromosome 22 and the proto-oncogene ABL locus of chromosome 9 to form a bcr/abl oncogenic protein (Tefferi et al. Mayo Clin Proc, 80(3):390-402, 2005). Although the Philadelphia chromosome was first associated with CIVIL, it is now known to be an indicator of prognosis in other blood disorders such as acute lymphoblastic leukemia (ALL).

A "gene translocation breakpoint" as used herein refers to a position in a gene sequence wherein the wild type sequence is disrupted and the portion of the gene either upstream or downstream of the position (the breakpoint) is deleted or translocated to a different place in the genome (i.e., breaks apart from the remainder of the gene and incorporates into the genome at a different position).

General Overview of the Technology

Disclosed herein is a method of detecting the presence or absence of a target gene dysregulation in a sample. Also disclosed is a method of diagnosing or monitoring cancer such as, for example, non-small cell lung cancer (NSCLC). Additional exemplary cancers include thyroid cancer (including but not limited to papillary thyroid cancer), bone and soft tissue sarcomas, and any of various leukemias and lymphomas (such as, for example, acute myeloid leukemia (AML)). In some embodiments, the disclosed methods of the invention re performed on a sample obtained from a subject in need of a determination regarding the presence or absence of a gene translocation.

The method described herein generally provides for the detection, measuring, and comparison of gene expression levels of different regions of a target gene within a test sample. Accordingly, the technology relates to detecting and/or monitoring a sample containing a messenger RNA of a target gene to determine the expression level of a 5' region of the target gene and a 3' region of the target gene. As used herein, the phrases "detecting the amount" or "detecting the level" refer to observing a signal from a detectable label that indicates the quantity of transcript from any gene or portion of a gene, such as a 5' region of a gene, a 3' region of the target gene, or a reference gene. The amount can be expressed as a concentration, as a number of copies, or as a cycle threshold (Ct) value, for example. As used herein, a "cycle threshold" for an analyte is the PCR cycle at which the detection signal (for example, a fluorescence signal) crosses a specified detection threshold (such as, for example, a fluorescence threshold) when performing real-time nucleic acid amplification. The Ct depends on the amplification reaction efficiency which includes starting template copy number, organism lysis, PCR amplification, hybridization or cleavage of fluorogenic probe and sensitivity of detection.

Detecting the level or amount of gene expression does not require the method to provide 100% sensitivity and/or 100% specificity. As is well known, "sensitivity" is the probability that a test is positive, given that the subject has a target nucleic acid sequence, while "specificity" is the probability that a test is negative, given that the subject does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

The disclosed method exploits intragenic differential expression (IDE) exhibited when either the 5' portion of a gene or the 3' portion of a gene is deleted or translocates to another location within the genome. A gene that undergoes such a rearrangement will exhibit differential expression of the 5' gene region relative to the 3' gene region. The 5' region of a target gene is the portion of the target gene that is upstream of the gene translocation breakpoint and the 3' region of a target gene is the portion of the target gene that is downstream of the gene translocation breakpoint. In some embodiments, term "5' region" refers to the portion of a polynucleotide located towards the 5' end of the polynucleotide relative to the 3' region, and may or may not include the 5' most nucleotide(s) of the same polynucleotide. In the context of translocations, the 5'-region refers to a region that is in the 5' direction or upstream of a translocation breakpoint. In the context of the present methods, the 5' region may be located near the 5' end of the transcribed portion of the target gene. In some embodiments, the 5' region encompasses all or a portion of the 5' untranslated region (UTR) of the target gene. In other embodiments, the 5' region is located downstream of the start codon (if the target gene is a protein-coding gene); for example, at least 10, at least 50, at least 100, at least 200, or at least 500 nucleotides downstream of the stop codon. The size of the 5' region to be amplified can vary depending on the detection method chosen. In some embodiments, the primers may be selected to amplify at least 10, at least 20, at least 30, at least 50, at least 100, at least 200, or at least 500 nucleotides in the 5' region.

In some embodiments, the term "3' region" refers to the portion of a polynucleotide located towards the 3' end of the polynucleotide relative to the 5' region, and may or may not include the 3' most nucleotide(s) of the same polynucleotide. In the context of translocations, the 3'-region refers to a region that is in the 3' direction or downstream of a translocation breakpoint. In the context of the present methods, the 3' region may be located near the 3' end of the transcribed portion of the target gene. In some embodiments, the 3' region encompasses all or a portion of the 3' UTR of the target gene. In other embodiments, the 3' region is located upstream of the stop codon (if the target gene is a protein-coding gene); for example, at least 10, at least 50, at least 100, at least 200, or at least 500 nucleotides upstream of the stop codon. The size of the 3' region to be amplified can vary depending on the detection method chosen. In some embodiments, the primers may be selected to amplify at least 10, at least 20, at least 30, at least 50, at least 100, at least 200, or at least 500 nucleotides in the 3' region.

When assessing known genetic abnormalities, the terms "5'-region" and "3'-region" are somewhat relative in that each region is selected to be on a different side of the defect (e.g., breakpoint) that results in the genetic abnormality. These regions may be selected for convenience or other substantive reasons (i.e., simultaneous assessment of other abnormalities such as mutations (SNPs), deletions, insertions, and the like) and need not be at the 5'- and 3'-termini, respectively, of the transcript. It is preferable that, when assessing target nucleic acids for unknown transcripts (i.e., a specific breakpoint has not been previously identified), the distance between the 5' region and the 3' region for a particular target gene should be maximized to the greatest extent possible to allow for the detection of a variety of chromosomal abnormalities that may occur between the two regions. This strategy maximizes the possibility that any breakpoint associated with a genetic abnormality occur between the two regions. In one embodiment, one or both of the 5'- and 3'-regions assessed by the methods of this invention are located in the untranslated regions (UTRs) of the transcripts. Guidelines for selecting primers for PCR amplification are well known in the art. See, e.g., McPherson et al., PCR Basics: From Background to Bench, Springer-Verlag, 2000. A variety of computer programs for designing primers are available, e.g., Oligo (National Biosciences, Inc, Plymouth Minn.), MacVector (Kodak/IBI), and the GCG suite of sequence analysis programs (Genetics Computer Group, Madison, Wis. 53711).

An exemplary IDE is one that occurs in situations where the 5' region of a gene remains under the control of the gene's normal regulatory elements, e.g., those elements contained in the 5' untranslated region (UTR) while the 3' region of the gene translocates and becomes juxtaposed so as to be under the control of different regulatory elements or none at all. For these types of mutations, the 5' region of the gene is expressed according to the target gene's own regulatory elements, while the 3' gene region will not be expressed (in the case where the 3' region is deleted or translocated to a position that is not actively expressed) or will be expressed at a level consistent with the regulatory elements of a different gene.

The IDE method disclosed herein employs two or more primers, primer pairs and/or probes that span various portions of a target gene 5' region and two or more additional primers, primer pairs and/or probes that span various portions of the target gene 3' regions. A combination of multiple primers, primer pairs and/or probes is identified to amplify portions of each of the 5' gene region and the 3' gene region and the IDE may be expressed as ΔCt, which is calculated based on the average Ct values among the multiple primers in the 5' and 3' regions. In some embodiments, three, four, five, six, or more primers, primer pairs and/or probes are employed for each of the 3' and 5' gene regions.

In one embodiment, an IDE Score can be calculated according to the following formula:

$$\text{IDE Score} = \Delta Ct = (\text{avgCt}_{5'} - \text{avgCt}_{3'})$$

wherein ΔCt is the difference between the average Ct values for the primers directed to the 5' gene region (avgCt$_{5'}$) and the average Ct values for the primers directed to the 3' gene region (avgCt$_{3'}$). See FIG. 1. In this embodiment the avgCt$_{5'}$ is higher (reflecting a lower copy number) than the avgCt$_{3'}$ when a specimen is translocation-positive. Ct values are inversely proportional to expression levels such that when 3' expression levels are greater than 5' expression levels, the avgCt$_{3'}$ level will be less than the avgCt$_{5'}$. Ct values can be obtained by real-time PCR and determined as the PCR cycle at which the fluorescence signal for each primer crosses a specified fluorescence threshold.

The inventors of the present invention surprisingly discovered that calculating a ΔCt from the average Ct of multiple primers or primer pairs for the 3' target gene region and the average Ct of multiple primers or primer pairs for the 5' target gene region resulted in superior assay performance. In fact, when two or more primers or primer pairs are used to amplify multiple portions of each of the 3' target gene region and the 5' target gene region and the ΔCt is calculated from the average Ct of the multiple primers or primer pairs for each region, it was observed that assay sensitivity, specificity, negative predictive value (NPV) and positive predictive value (PPV) were such that the IDE assay could be used effectively as a screening tool for translocation such that IDE-negative samples are truly negative for gene translocation and IDE-positive samples are putative positive for gene translocation. If desired, the designation of samples as IDE-positive using the method disclosed herein can be further confirmed by subsequent FISH or other molecular assays.

In addition, it was also surprisingly discovered that the use of multiple primers and/or probes overcame a problem associated with other methods wherein certain samples do not amplify well, resulting in high false positive and false negative rates. By employing multiple primers and/or probes directed to each of the 5' region and 3' region of a target gene, the IDE design disclosed herein exhibits greatly reduced false positive and false negative rates and superior assay sensitivity and specificity as compared to methods wherein only a single primer pair is employed for each region (i.e. the 3' region and the 5' region).

In some embodiments, the best primers, primer pair(s) and/or probe(s) is identified for each of the 5' region and the 3' region and the IDE score is calculated based on the 3' gene expression level and the 5' gene expression as determined using those primers and/or probes. In some embodiments, multiple primers or primer pairs are employed for each region (i.e., the 3' region and the 5' region) and the IDE score is calculated from the average level of expression for each region as determined from the signals detected with the multiple primers or primer pairs for each region.

In some embodiments, an IDE Score (ΔCt) is calculated as the difference between the average cycle threshold among the 5' target primer pairs and the average cycle threshold among the 3' target primer pairs, and the test sample is identified as having a target gene dysregulation if the IDE Score is significantly different than a pre-determined cutoff value and the difference indicates the severity of a target gene dysregulation. A "cutoff value" signifies the IDE (or ΔCt) value at or above which a sample is identified as fusion positive. The "cutoff" value is determined from the ranges of IDE scores of known fusion positive and fusion negative samples. In some embodiments, the cut-off for positivity is calculated as ΔCt>2, >4, >5, >8, or >10 between 5' and 3'.

Thus, the disclosed method provides for detecting mutations that result in the differential expression of the 5' region of a gene relative to the 3' region of the gene. One example of this situation occurs in some NSCLC patients who have a translocation of a ALK, ROS1 or RET gene such that the 5' region of the gene remains under the control of the promoter normally associated with the target gene, but the 3' gene region is translocated such that it is expressed by a much more robust promoter that is associated with a different gene.

Specimens that do not contain a chromosomal abnormality within a target gene will demonstrate the same expression pattern between the 5' region and the 3' region because they are linked in a unimolecular fashion. However, when the target gene is affected by some genetic or chromosomal abnormality, the 5' and 3' regions may show independent expression patterns for the 5' and 3' regions. In the case of a translocation, the 5' and 3' regions will show different expression patterns because these two regions are now unlinked on the chromosome.

As used herein, the phrases "difference of the level," "difference in amounts," and "difference in expression patterns" refer to differences in the quantity of transcript from the 5' region of a gene compared to the quantity of transcript from the 3' region of the target gene. In one embodiment, a transcript from the 5' region of a gene is present at an elevated amount or at a decreased amount in a sample compared to the amount of transcript from the 3' region of the target gene. In wild-type or normal cells, the quantity of transcript of the 5' region of the target gene and the quantity of transcript from the 3' region of the target gene is expected to be at equal or near-equal quantities. By equal quantity, it is meant that the measured amounts of transcript or detectable signal (which correlates to the amount of transcript) for the 5' region and the 3' region do not exhibit a statistically significant difference from the same comparison in control samples. Methods for comparing these values are known to those of skill in the art and include, but are not limited to, a Student's t-test and ANOVA analysis. The artisan recognizes that, because of technical differences inherent in the detection methodologies used herein, the amount of detectable signal from the 5'-region may not necessarily be equal to the amount of detectable signal from the 3'-region even though no chromosomal abnormality is present (i.e., both regions remain linked in a unimolecular manner and under the control of the same regulatory elements).

Distinct 3'-target gene expression levels expected to be found in samples containing target gene translocations and those without translocations can be established by normalizing the expression levels of 3' target gene to 5' target gene.

In some embodiments, each 3'- and 5'-target expression level measurement may be normalized to an endogenous control gene (Ct$_{control}$), and the average of the normalized measurements used when calculating an IDE score. Some useful formulae include, for example:

$$IDE = \Delta Ct = [avg(Ct_{5'}/Ct_{control})] - [avg(Ct_{3'}/Ct_{control})],$$
and $$IDE = \Delta Ct = Ln[avg(Ct_{5'}/Ct_{control})] - Ln[avg(Ct_{3'}/Ct_{control})]$$

In some embodiments a ΔCt≥4 indicates the presence of target gene fusion products. In some embodiments, a ΔCt≥2, 4.5, 5, or 8, indicates the presence of target gene fusion products.

In other embodiments, the measured amount of the 3'- and 5'-transcripts in the test sample may be normalized to the level of the same transcripts from a control sample, rather than an endogenous gene.

The IDE Score may be expressed as a as a "relative amount" or "ratio" of the expression of the 5' region of the target gene relative to the 3' region of the target gene.

Relative amounts may be a single value or a range of values. The expression of each region (either the 5' region or the 3' region) is determined as the average Ct of transcripts from the multiple primers, primer pairs and/or probes directed to that region of the target gene. If the ratio of the average expression of the 5' region of the target gene relative to the average expression of the 3' region of the target gene is statistically less than or greater than 1, then a chromosomal abnormality is detected. Where the ratio is less than 1, the 3' region of the target gene has been translocated to a genomic region that is more transcriptionally active than the native target gene. Where the ratio is greater than 1, the 3' region has either been deleted or translocated to a genomic region that is less transcriptionally active than the native target gene. In either case, a ratio that is significantly different than 1 will indicate differential expression and one could conclude that the 5' and 3' regions of the target gene are being expressed under the control of different promoters (or one region may not be expressed at all), such that there is a chromosomal abnormality in the target gene.

In some embodiments, if the average amount of transcript or detectable signal for the 5' region and the 3' region are within about 1 standard deviation, within about 0.5 standard deviations, within about 0.2 standard deviations, within about 0.1 standard deviations, or within about 0.01 standard deviations, then there may be no significant difference between the two amounts. In this example, one could conclude that the 5' and 3' regions are expressed in a unimolecular fashion and there is no chromosomal abnormality in the target gene.

Alternatively, if the average amount of transcript or detectable signal for the 5' region and the 3' region exceed about 1 standard deviation, about 1.5 standard deviations, about 2.0 standard deviations, or about 2.5 stand deviations, then there may be a significant difference between the two amounts. In such a case, one could conclude that the 5' and 3' regions are expressed under the control of different promoters (or one region may not be expressed at all), such that there is a chromosomal abnormality in the target gene.

An additional advantage of the disclosed IDE method as compared to other methods is that a standard curve need not be generated to practice the disclosed method. Thus, the assay design process is simplified by eliminating the needs to design standards for each target gene that amplifies equally at both the 5' and 3'.

Multiple primers and/or primer pairs directed to each of the 5' region and the 3' region of multiple genes may be employed to screen a translocation panel of genes for a particular disease or disorder.

A sample obtained from a subject may be assayed using reverse-transcription-polymerase chain reaction (RT-PCR) and/or real-time polymerase chain reaction (real-time PCR) to determine the relative expression levels of the 5' and 3' regions of a particular gene or nucleic acid sequence of interest. RT-PCR is a sensitive technique for mRNA detection and quantitation. Compared to the two other commonly used techniques for quantifying mRNA levels, Northern blot analysis and RNase protection assays, RT-PCR can be used to quantify mRNA levels from much smaller samples. In fact, this technique is sensitive enough to enable quantitation of RNA from a single cell.

One of skill in the art would know how to design oligonucleotide primers and probes for use to detect differential 5' and 3' expression from any gene of interest, provided the sequence of the gene of interest is known. The size of the primer will depend on many factors, including the ultimate function or use of the oligonucleotide. An oligonucleotide that functions as an extension primer or probe, for example, will be sufficiently long to prime the synthesis of extension products in the presence of a catalyst, e.g., DNA polymerase, and deoxynucleotide triphosphates.

Alternatively, an insertion or transposition event can lead to the differential expression of the 5' region and the 3' region of a target gene. The insertion of, for example, a promoter or other regulatory element, or the transposition of a transposable element into the middle of the coding sequence of a gene of interest can create a situation where the 5' region of the target gene is expressed at a different level than the 3' region of the target gene.

Any such mutation that results in the differential expression of a 5' region of a target gene and the 3' region of the target gene is detectable according to the methods, compositions and kits described herein. One of skill in the art would know how to directed, for example, PCR primers to a 5' region of a gene of interest that occurs at or near the start of transcription, thereby ensuring a product corresponding to a region that is 5' (upstream) of a potential chromosomal abnormality. One of skill in the art need only refer to the known sequence of the target gene and known base-pairing rules to determine an effective PCR primer or primer pair.

Likewise, one of skill in the art could design a primer or primer pair directed to a 3' region of the gene of interest. In particular examples, where a known chromosomal abnormality occurs, one of skill in the art is further aided by the knowledge of a known mutation site, thereby allowing the design of primers that are at or near the mutation site, e.g., a primer or primer pair could be designed immediately 5' (upstream) of the mutation site and immediately 3' (downstream) of the mutation site; or the primer or primer pairs could be designed, for example, within about 5 nucleotides (nt) of the mutation site on either side, within about 10 nt of the mutation site on either side, within about 20 nt of the mutation site on either side, within about 50 nt of the mutation site on either side, within about 100 nt of the mutation site on either side, within about 250 nt of the mutation site on either side or within about 500 nt of the mutation site on either side.

In certain embodiments, IDE methods disclosed herein allow for detection of translocations irrespective of the chromosomal breakpoint.

Chromosomal Abnormalities:

A chromosomal abnormality may reflect a difference between the full genetic complement or any portion thereof, of an organism, as compared to a normal full genetic complement of all chromosomes in that organism. For example, a genetic abnormality may include a change in chromosomal copy number (e.g., aneuploidy), or a portion thereof (e.g., deletions, duplications, amplifications); or a change in chromosomal structure (e.g., translocations, point mutations). A genetic abnormality may lead to pathological conditions. While some diseases, such as cancer, are clue to chromosomal abnormalities acquired in a few cells during life, the term "genetic disease" most commonly refers to diseases present in all cells of the body and present since conception. Genetic abnormalities may be hereditary or non-hereditary.

Genetic duplication is any duplication of a region of the genomic sequence. It may occur as an error in homologous recombination, a retrotransposition event, or duplication of an entire chromosome. Duplication of a gene has been associated with several diseases such as some cases of pagetic osteosarcoma is associated with duplication of MYC gene (Sarcoma, 1(3-4):131-134, 1997), some cases of breast cancer are associated with duplication of HER-2/neu gene (Ann Oncol., 12(suppl 1):S3-S8, 2001), some cases of bladder tumor are associated with duplication of c-erb-2 gene (Cancer Res., 55:2422-2430, 1995).

A deletion (also called gene deletion, deficiency, or deletion mutation) is a genetic aberration in which a part of a chromosome or a sequence of DNA is missing. Deletion is the loss of genetic material. Any number of nucleotides can be deleted, from a single base to an entire piece of chromosome. Deletions can be caused by errors in chromosomal crossover during meiosis. Deletions are associated with an array of genetic disorders, including some cases of male infertility and two thirds of cases of Duchenne muscular dystrophy, a deletion of part of the short aim of chromosome 5 results in a syndrome called Cri du chat, also known as "cry of the cat" syndrome.

Genetic abnormalities may also be point mutations insertions, or deletions. A point mutation, or substitution, is a type of mutation that causes the replacement of a single base nucleotide with another nucleotide. Insertion and deletion includes insertions or deletions of a single base pair. Mutations in the gene or chromosome often are associated with diseases such as sickle cell anemia, cystic fibrosis, hemophilia, phenylketonuria, spina bifida, etc.

Sample Preparation

The samples disclosed herein that may be analyzed according to the present invention include, but not limited in any way to, blood (whole blood or a fraction of blood such as plasma, serum, or particular cell fractions), lymph, mucus, tears, saliva, cystic fluid, urine, semen, stool, cerebrospinal fluid (CSF), ascites fluid, and biopsy samples of body tissue, fine needle aspirate (FNA), bronchalveolar lavage (BAL). Additional specimens from which target nucleic acids can be detected and quantified with the methods of the present invention may be obtained from subjects according to methods known to those of skill in the art synovial fluid, pleural fluid, pericardial fluid, intraocular fluid, tissue biopsies or endotracheal aspirates, sputum, swabs from, e.g., skin, inguinal, nasal and/or throat. Methods of obtaining test samples and reference samples are well known to those of skill in the art and include, but are not limited to, aspirations, tissue sections, drawing of blood or other fluids, surgical or needle biopsies, collection of paraffin embedded tissue, collection of body fluids, collection of stool, and the like. In one embodiment, the test sample may be obtained from an individual who is suspected of having a disease (such as, for example, cancer) or a genetic abnormality. In some embodiments, specimens are tissue samples (biopsy samples) from a subject having or suspected of having a disease or a genetic abnormality.

The nucleic acid (DNA and/or RNA) may be isolated from the sample according to any methods well known to those of skill in the art. If necessary, the sample may be collected or concentrated by centrifugation and the like. The cells of the sample may be subjected to lysis, such as by treatments with enzymes, heat surfactants, ultrasonication or combinations thereof. The lysis treatment is performed in order to obtain a sufficient amount of RNA derived from the cells of interest, if present in the sample, to detect using RT-PCR and/or real-time PCR. Nucleic acid need not be extracted, but may be made available by suitable treatment of cells or tissue such as described in US Patent Publication No. 2008/131876.

In one embodiment, mRNA or cDNA generated from mRNA or total RNA may be used. Various methods of RNA extraction are suitable for isolating the RNA. Suitable methods include phenol and chloroform extraction. See Maniatis et al., Molecular Cloning, A Laboratory Manual, 2d, Cold Spring Harbor Laboratory Press, page 16.54 (1989), In addition kits for isolating mRNA and synthesizing cDNA are commercially available e.g., RNeasy Protect Mini kit, RNeasy Protect Cell Mini kit from Qiagen.

In one embodiment, a dual RNA/DNA isolation method is used employing a trizol based reagent for initial isolation of RNA and DNA from patient samples. Upon contact with patient samples, the phenol and high salt reagents in the trizol effectively inactivate any disease agent or secondary disease agent that may be present in the patient sample. After the RNA and DNA are isolated from the patient samples, a silica based column may be used to further isolate the RNA and DNA. The use of silica based columns allows for wash steps to be performed quickly and efficiently while minimizing the possibility of contamination. The wash steps may be used to remove PCR and RT-PCR inhibitors. The column method for nucleic acid purification is advantageous as it can be used with different types of patient samples and the spin and wash steps effectively remove PCR or RT-PCR inhibitors.

Amplification of Nucleic Acids

Nucleic acid samples or target nucleic acids may be amplified by various methods known to the skilled artisan. In suitable embodiments, PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase. In the present methods, at least two primer pairs are used to amplify two different portions of the 5' region of a transcript. At least two primer pairs also are used to amplify two different portions of the 3' region of a transcript. In some embodiments, three, four, five or six different primer pairs are used to amplify different portions of the 5' region and/or 3' region. "Different portions" or "different parts" of a 5' region or of a 3' region refers to regions of the gene transcript having nucleotide sequences that are not identical to one another. Different regions may overlap with one another.

In one embodiment, the target nucleic acids are amplified in a multiplex amplification reaction. A variety of multiplex amplification strategies are known in the art and may be used with the methods of the invention. The multiplex amplification strategy may use PCR, RT-PCR or a combination thereof depending on the type of nucleic acid contained in the disease agent(s). For example, if an RNA genome is present, RT-PCR may be utilized. The PCR enzyme may be an enzyme with both a reverse transcription and polymerase function. Furthermore, the PCR enzyme may be capable of "hot start" reactions as is known in the art.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the target nucleic acid to form reaction products, excess primers will bind to the target nucleic acid and to the reaction products and the process is repeated, thereby generating amplification products. Cycling parameters can be varied, depending on the length of the amplification products to be extended. An internal positive amplification control (IC) can be included in the sample, utilizing oligonucleotide primers and/or probes.

Detection of Amplified Nucleic Acids.

Amplification of nucleic acids can be detected by any of a number of methods well-known in the art such as gel electrophoresis, column chromatography, hybridization with a probe, sequencing, melting curve analysis, or "real-time" detection.

In one approach, sequences from two or more fragments of interest are amplified in the same reaction vessel (i.e., "multiplex PCR"). Detection can take place by measuring the end-point of the reaction or in "real time." For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TAQMAN™ system, the SCORPION™ bi-functional molecule, and the use of intercalating dyes for double stranded nucleic acid.

In end-point detection, the amplicon(s) could be detected by first size-separating the amplicons, then detecting the size-separated amplicons. The separation of amplicons of different sizes can be accomplished by, for example, gel electrophoresis, column chromatography, or capillary electrophoresis. These and other separation methods are well-known in the art. In one example, amplicons of about 10 to about 150 base pairs whose sizes differ by 10 or more base pairs can be separated, for example, on a 4% to 5% agarose gel (a 2% to 3% agarose gel for about 150 to about 300 base pair amplicons), or a 6% to 10% polyacrylamide gel. The separated nucleic acids can then be stained with a dye such as ethidium bromide and the size of the resulting stained band or bands can be compared to a standard DNA ladder.

In another embodiment, two or more fragments of interest are amplified in separate reaction vessels. If the amplification is specific, that is, one primer pair amplifies for one fragment of interest but not the other, detection of amplification is sufficient to distinguish between the two types—size separation would not be required.

In some embodiments, amplified nucleic acids are detected by hybridization with a specific probe. Probe oligonucleotides, complementary to a portion of the amplified target sequence may be used to detect amplified fragments. Hybridization may be detected in real time or in non-real time. Amplified nucleic acids for each of the target sequences may be detected simultaneously (i.e., in the same reaction vessel) or individually (i.e., in separate reaction vessels). In some embodiments, the amplified DNA is detected simultaneously, using two or more distinguishably-labeled, gene-specific oligonucleotide probes, one which hybridizes to the first target sequence and one which hybridizes to the second target sequence.

The probe may be detectably labeled by methods known in the art. Useful labels include, e.g., fluorescent dyes (e.g., CY5™, CY3™, FITC, rhodamine, lanthamide phosphors, Texas red, FAM, JOE, Cal Fluor Red 610®, Quasar 670 ™), $^{32}P$, $^{35}S$, $^{3}H$, $^{14}C$, $^{125}I$, $^{131}I$, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., DYNABEADS™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) that hybridizes or binds to the nucleic acid to be detected.

One general method for real-time PCR uses fluorescent probes such as the TaqMan® probes, molecular beacons, and Scorpions™. Real-time PCR quantitates the initial amount of the template with more specificity, sensitivity and reproducibility, than other forms of quantitative PCR, which detect the amount of final amplified product. Real-time PCR does not detect the size of the amplicon. The probes employed in SCORPION™ and TAQMAN® technologies are based on the principle of fluorescence quenching and involve a donor fluorophore and a quenching moiety.

In one embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e. collisional) quenching or by Forster or fluorescence resonance energy transfer ("FRET"). Quenching by FRET is generally used in TAQMAN™ probes while proximal quenching is used in molecular beacon and SCORPION™ type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from decreased distance between the donor and the quencher (acceptor fluorophore).

Suitable fluorescent moieties include the following fluorophores known in the art: 4-acetamido-4'-isothiocyanatostilbene-2,2' disulfonic acid, acridine and derivatives (acridine, acridine isothiocyanate) Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (*Lucifer* Yellow VS), N-(4-anilino-1-naphthyl)maleimide, anthranilamide, Black Hole Quencher (BHQ™) dyes (Biosearch Technologies), BODIPY® R-6G, BODIPY® 530/550, BODEPY® FL, Brilliant Yellow coumarin and derivatives (coumarin, 7-amino-4-methylcoumarin (AMC, Coumarin 120), 7-amino-4-trifluoromethylcouluarin (Coumarin 151)), Cy2®, Cy3®, Cy3.5®, Cy5®, Cy5.5®, cyanosine, 4',6-diaminidino-2-phenylindole (DAPI), 5',5'''-dibromopyrogallol-sulfonephthalein (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse (Epoch Biosciences Inc.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET)), fluorescamine, IR144, IR1446, Malachite Green isothiocyanate, 4-methylumbelliferone, ortho cresolphthalein, nitrotyrosine, pararosaniline, Phenol Red, B-phycoerythrin, R-phycoerythrin, o-phthaldialdehyde, Oregon Green®, propidium iodide, pyrene and derivatives (pyrene, pyrene butyrate, succinimidyl 1-pyrene butyrate), QSY® 7, QSY® 9, QSY® 21, QSY® 35 (Molecular Probes), Reactive Red 4 (Cibacron® Brilliant Red 3B-A), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red)), N,N,N',N'-tetramethyl-6-carboxyrhodamine (TAMRA), tetramethyl rhodamine, tetramethyl rhodamine isothiocyanate (TRITC), CAL Fluor Red 610, Quasar 670, riboflavin, rosolic acid, terbium chelate derivatives.

Other fluorescent nucleotide analogs can be used, see, e.g., Jameson, 278 Meth. Enzymol., 363-390 (1997); Zhu, 22 Nucl. Acids Res., 3418-3422 (1994). U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield, Mol. Cell Probes, 9:145-156 (1995). Detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, and then incorporated into nucleic acids during nucleic acid synthesis or amplification.

With Scorpion™ probes, sequence-specific priming and PCR product detection is achieved using a single molecule. The Scorpion™ probe maintains a stem-loop configuration in the unhybridized state. The fluorophore is attached to the 5' end and is quenched by a moiety coupled to the 3' end The 3' portion of the stem also contains sequence that is complementary to the extension product of the primer. This sequence is linked to the 5' end of a specific primer via a non-amplifiable monomer. After extension of the Scorpion™ primer, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion™ resulting in an extension product. A fluorescent signal is generated due to the separation of the fluorophore from the quencher resulting from the binding of the probe element of the Scorpion™ to the extension product.

TAQMAN® probes (Heid et al., Genome Res, 6:986-994, 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi et al., Nature Biotechnology, 16:49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TAQMAN® probes are designed to anneal to an internal region of a PCR product. When the polymerase (e.g., reverse transcriptase) replicates a template on which a TAQMAN® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

In a suitable embodiment, real-time PCR is performed using any suitable instrument capable of detecting fluorescence from one or more fluorescent labels. For example, real time detection on the instrument (e.g., an ABI Prism® 7900HT sequence detector) monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually. The Ct value may be correlated to the amount of initial template nucleic acid in the reaction.

In some embodiments, melting curve analysis may be used to detect an amplification product. Melting curve analysis involves determining the melting temperature of nucleic acid amplicon by exposing the amplicon to a temperature gradient and observing a detectable signal from a fluorophore. Melting curve analysis is based on the fact that a nucleic acid sequence melts at a characteristic temperature called the melting temperature ($T_m$), which is defined as the temperature at which half of the DNA duplexes have separated into single strands. The melting temperature of a DNA depends primarily upon its nucleotide composition. Thus, DNA molecules rich in G and C nucleotides have a higher $T_m$ than those having an abundance of A and T nucleotides.

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. In some embodiments, the fluorescent dye for determining the melting temperature of a nucleic acid may be excited by different wavelength energy than any other of the different fluorescent dyes that are used to label the oligonucleotides. In some embodiments, the second fluorescent dye for determining the melting temperature of the detected nucleic acid is an intercalating agent. Suitable intercalating agents may include, but are not limited to SYBRT™ Green 1 dye, SYBR™ dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1 YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1. JO-PRO-1, and mixture thereof. In suitable embodiments, the selected intercalating agent is SYBR™ Green 1 dye.

By detecting the temperature at which the fluorescence signal is lost, the melting temperature can be determined. In the disclosed methods, each of the amplified target nucleic acids may have different melting temperatures. For example, each of these amplified target nucleic acids may have a melting temperature that differs by at least about 1° C., more preferably by at least about 2° C., or even more preferably by at least about 4° C. from the melting temperature of any of the other amplified target nucleic acids.

Methods of Diagnosis

In one aspect, the methods described herein provide for diagnosing prostate cancer or a susceptibility to cancer in a subject. The term "diagnose" or "diagnosis" as used herein refers to the act or process of identifying or determining a disease or condition in an organism or the cause of a disease or condition by the evaluation of the signs and symptoms of the disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease, i.e., there may be differential diagnoses that can be inferred from a diagnostic factor or symptom. Likewise, there may be instances where a factor or symptom that is indicative of a particular disease is present in an individual that does not have the particular disease. The methods include, but are not limited to, prostate and lung cancer and translocations, insertions, inversions and deletions associated with those cancers.

In one embodiment, the expression level of the 5' region of the ROS1 gene is compared to the expression level of the 3' region of the ROS1 gene in a sample from a subject, wherein a difference in the expression levels of the 5' region of the ROS1 gene and the 3' region of the ROS1 gene is indicative of NSCLC or a susceptibility to NSCLC in the subject.

In another embodiment, the expression level of the 5' region of the RET gene is compared to the expression level of the 3' region of the RET gene in a sample from a subject, wherein a difference in the expression levels of the 5' region of the RET gene and the 3' region of the RET gene is indicative of NSCLC or a susceptibility to NSCLC in the subject.

In one embodiment, the expression level of the 5' region of the ALK gene is compared to the expression level of the 3' region of the ALK gene in a sample from a subject, wherein a difference in the expression levels of the 5' region of the ALK gene and the 3' region of the ALK gene is indicative of NSCLC or a susceptibility to NSCLC in the subject.

Methods of Prognosis

In one aspect, the methods described herein provide a prognosis for cancer or in a subject. The term "prognosis" as used herein refers to a prediction of the probable course and outcome of a clinical condition or disease. A prognosis of a patient is usually made by evaluating factors or symptoms of a disease that are indicative of a favorable or unfavorable course or outcome of the disease. The term prognosis does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example prognosis can be expressed as a percent chance that a patient will survive after one year, five years, ten years or the like. Alternatively prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time. The methods include, but are not limited to, prostate and lung cancer.

A prognosis is often determined by examining one or more prognostic factors or indicators. These are markers, such as the presence of a particular chromosomal translocation, the presence or amount of which in a patient (or a sample obtained from the patient) signal a probability that a given course or outcome will occur. The skilled artisan will understand that associating a prognostic indicator with a predisposition to an adverse outcome may involve statistical analysis.

In one embodiment, the expression level of the 5' region of the ROS1 gene is compared to the expression level of the 3' region of the ROS1 gene in a sample from a subject, wherein a difference in the expression levels of the 5' region of the ROS1 gene and the 3' region of the ROS1 gene is indicative of stage, severity or outcome of prostate cancer in the subject.

Kits

In another aspect, the disclosure provides a kit for detecting a genetic abnormality in a sample. The kit may include: (a) at least two primer pairs directed to different regions of a 5' portion of a target gene transcript, and (b) at least two primer pairs directed to different regions of a 3' portion of a target gene transcript. The kit may, optionally, further contain at least one probe directed to at least one amplicon sequence that results from amplification with the primers in the kit. In some embodiments, the at least one primer in each primer pair is detectably labeled and/or is a primer-probe.

In one embodiment, the target gene is ROS1, RET or ALK. In some embodiments, primer pairs directed to each of the 3' target gene transcripts are present in the kit.

In some embodiments the kit further comprises one or more reagents such as, for example, reagents used for performing reverse transcription, PCR, and/or real-time PCR. In some embodiments a kit comprises printed instructions.

As used herein, a "kit" refers to a packaged collection of components used for a specific purpose. Non-limiting examples of materials in which a kit may be packaged include boxes, bags, envelopes and tubes, but kit components may be supplied to a consumer in additional types of packaging materials. In some embodiments, the primers and/or probes included in a kit are isolated polynucleotides and may be supplied in tubes, vials or other types of containers within the kit. In some embodiments a kit further contains instructions for using the kit components. The instructions may be printed on a material within the kit or supplied in electronic format. In some embodiments, the printed instructions specify how to use the reagents contained in the kit to detect intragenic differential expression.

EXAMPLES

Example 1—Intragenic Differential Expression (IDE) Assay for a ALK+ROS1+RET Translocation Panel The examples below illustrate a standard protocol for performing real-time PCR and analyzing in real time. The TaqMan system of probe labeling is an exemplary method of real time detection of PCR amplicons. The following examples serve to illustrate the present invention and is in no way intended to limit the scope of the invention.

Ide Protocol:

Multiple primer/probe pairs were designed targeting different 5' (before translocation breakpoints) and 3' (after translocation breakpoints) regions of ALK, ROS1, and RET (Table 1). Extracted RNA was first reverse transcribed into cDNA using Superscript III (Life Technologies), then mixed with sequence-specific forward/reverse primers (IDT, Coralville, Iowa), and 2×PCR Master Mix (Celera, Alameda, Calif.). The mixture was subjected to 45 cycles of PCR amplification (95° C. for 15 sec, then at 60° C. for 60 sec) on either BioMark HD Gene Expression 48.48 Array Chip (Fluidigm, South San Francisco, Calif.) or ViiA7 instrument (Life Technologies, Carlsbad, Calif.). The ΔCt was calculated and a high IDE score (ΔCt≥4.0) implicates the presence of target gene fusion products.

TABLE 1

Primer design for Intragenic differential expression (IDE) multiplex RT-PCR assay.

| | Forward | Reverse |
|---|---|---|
| ALK5A | GATGGACTTGCTGGATGGG | ATGGTGTGCTTGGAGTCAG |
| ALK5B | ATCTGCTTCTGTGACCACG | AGAGGATCAGCGAGAGTGG |
| ALK5C | CCCTGAAAGGCATCCAGATC | TCATGGTGTTCTTCCCGC |
| ALK5D | CATCAGCCTGGACTGCTACCT | GGTGCTGTATTCTGCAGGATCTT |

TABLE 1-continued

Primer design for Intragenic differential expression (IDE) multiplex RT-PCR assay.

| | Forward | Reverse |
|---|---|---|
| ALK5E | CTTCCCTTTCCTGTCTCATCG | TTCCTGAGGTCATGCAGTG |
| ALK3A | TGTGGCTGTCAGTATTTGGAG | AGGTCAAGAGGCAGTTTCTG |
| ALK3B | CAAGACCTCCTCCATCAGTG | CCTTCATACACCTCCCCAAAG |
| ALK3C | GAATGCCCAACGACCCAAG | TCCATGAGGAAATCCAGTTCG |
| ALK3D | GAAGACAGGCCCAACTTTGC | CGGGTCCTGGGTGCAGTAT |
| ALK3E | GTGTATGAAGGCCAGGTGTC | CTGGTGGTTGAATTTGCTGATG |
| ROS15A | ACTCCCTCAGTGATGTCTTTTC | CCTGGCCCCTTAGATGTAAAG |
| ROS15B | CAGGCTCTTGTTCAATGGAAG | GCAGAAGGGCCTAATTCAAAG |
| ROS15C | CTCATCAGATTTTGGGTTGAGCTA | GCTGCATGAAGTTTTAACATGGTAA |
| ROS15D | CAGTCAATGTATTCACCTGTACA | TTTCAGAAGTACTCCAGGCTG |
| ROS15E | CACTTTTGGAACTCTGTAGATCAG | CCTCTTCATATGCACCTTCCG |
| ROS13A | AACAGTGGAGTCATAAATGAAAGC | TTCGTTTCCATTAAAGCAACTGG |
| ROS13B | CTATGTGCAAACAGGAGGGA | TCTTTGGTCGGGTTCTTGAG |
| ROS13C | TGTGTCTACTTGGAACGGATG | TCACTATCCGTGGACTGGTATA |
| ROS13D | CAGCAGTGGACATCTTAGGAGTTG | GGAACCCTTCTTCAAAGTCTTCAC |
| ROS13E | TGGACATCTTAGGAGTTGAAGTG | GGTCTGTGGAACCCTTCTTCAA |
| RET5A | TTGTGGAGACCCAAGACATC | CCATAGCCAGCTTTAATCCC |
| RET5B | CGTCTGCTGTTGCTGCTG | CTGGTCCACATACAGCTTCT |
| RET5C | AGCAGACCTCTAGGCAGG | GCCGTCTCTTGCTGACTG |
| RET5D | TGCCGCTGCTAGGCAAA | CCAGTAAGCATCCCTCGAGAA |
| RET5E | AAGGAGATGGCAAAGGGATC | ATGTTGATGTCTTGGGTCTCC |
| RET3A | AGGGTCGGATTCCAGTTAAAT | CCTAGGGTCACGATCTCC |
| RET3B | GTCCCGAGATGTTTATGAAGAG | TGCGTGGTGTAGATATGATCAAA |
| RET3C | GGATGCAGTATCTGGCCG | CTCAGCTACCAGGATGTTTC |
| RET3D | CCCACATGTCATCAAATTGTATGG | TTGGCGTACTCCACGATGAG |
| RET3E | GAAACATCCTGGTAGCTGAGG | TTTAACTGGAATCCGACCCTG |

TABLE 1-continued

Primer design for Intragenic differential expression (IDE) multiplex RT-PCR assay.

|  | Forward | Reverse |
|---|---|---|
| ABL1A | GCATGTTGGCAGTGGAATC | CGTCTGAGATACTGGATTCCTG |
| ABL1B | TCCTCCAGCTGTTATCTGGAAGA | TGGGTCCAGCGAGAAGGTT |
| ABL1C | GTCCTCGTCCTCCAGCTGTTA | GAGGCTCAAAGTCAGATGCTACTG |

FISH Protocol

Fluorescence in situ hybridization (FISH) was performed on a subset of samples. FFPE sections (4 µm thick) were hybridized with the Vysis ALK Break Apart FISH Probe (Abbott Molecular, Abbott Park, Ill.), ROS1 Breakapart probe (CytoCell, Cambridge, UK) and Poseidon RET Break Apart Probe (Kreatech, Amsterdam, NL). In brief, de-paraffinized tissue sections were pretreated with 1 M Sodium Thiocyanate solution in 70° C. followed by pepsin digestion (10 mg/mL) at 40° C. 104, of probe was applied to each dehydrated and air dried slide and co-denatured at 85° C. for 3 minutes followed by hybridization over night at 37° C. Post-hybridization wash was performed with 2×SSC/0.3% NP-40 at 72° C. Slides were mounted with DAPI I counterstain (Vector Laboratories Inc., Burlingame Calif.). FISH results were evaluated with a Nikon 50i fluorescence microscope (Nikon Corp., Tokyo, Japan). The images were captured using a CCD camera and Isis® imaging system (MetaSystems, Watertown, Mass.). A total of 50 cells were analyzed on all the normal cases and 100 cells on any abnormal cases. On all cases, the entire slide was examined for possible areas where rearrangements may have been missed. The cut-off for gene rearrangement for ALK, ROS1 and RET were 15%, 9% and 12%, respectively.

EML4-ALK Protocol

EML4-ALK by multiplex RT-PCR was performed as previously described (12). Briefly, RNA samples were amplified by multiplex RT-PCR with FAM-labeled primer. The RT-PCR products were then diluted, denatured, and size-fractionated by capillary electrophoresis in an ABI 3730 genetic analyzer (Applied Biosystems, Foster City, Calif.). Results were analyzed with GeneMapper software (Applied Biosystems).

RET-PTC Protocol

RET-PTC1, RET-PTC3 rearrangements were detected by real-time RT-PCR as previously described (13). Extracted RNA were reverse transcribed and then amplified by real-time PCR on ABI 7900 instrument (Life Technologies), and the result was analyzed by SDS software (Life Technologies).

Results:

PCR Efficiency for IDE Assays

Serial dilutions of various RNA standards (Raji for ABL, PC3 for ALK, HCC-78 for ROS1, TPC-1 for RET, and various clinical samples) were used to establish amplification efficiency for IDE assays (Table 2). A total 18 primer pairs were selected for PCR efficiency test. All displayed good PCR efficiency (between 90~110%).

TABLE 2

IDE assay PCR amplification efficiency (selected primer pairs).

| Primer pair | Efficiency % |
|---|---|
| ALK5A | 97.6 |
| ALK5B | 98.8 |
| ALK5C | 92.2 |
| ALK3A | 94.1 |
| ALK3B | 97.7 |
| ALK3C | 95.3 |

| Primer pair | Efficiency % |
|---|---|
| ROS15A | 98.4 |
| ROS15B | 93.7 |
| ROS13A | 95.2 |
| ROS13B | 96.1 |
| ROS13C | 97.5 |
| ABL | 93.2 |

| Primer pair | Efficiency % |
|---|---|
| RET5A | 106.5 |
| RET5B | 94.7 |
| RET5C | 93.9 |
| RET3A | 91.5 |
| RET3B | 95.7 |
| RET3C | 96.9 |

IDE Result for Cell Line (Positive Control) Specimens:

RNA from translocation positive cell lines were studied in 9 separate setups and the result is summarized in Table 3. The result is 100% concordance between expected and observed, using a ΔCt≥4.0 between 5' and 3' as a cut-off for positivity.

TABLE 3

IDE assay performance: positive control cell line RNA.

| Cell ine RNA | IDE detection | Average Δ Ct |
|---|---|---|
| ALK POS (x1) | 16/16 (100%) | 10.51 (5.258~12.38) |
| ROS1 POS (x2) | 18/18 100% | 5.212 (4.152~5.847) |
| RET POS (x1) | 16/16 100% | 7.992 (5.778~11.34) |

ALK, ROS1, RET IDE Result Summary:

Next, a total of 408 NSCLC clinical samples were tested for ALK, ROS1, and RET translocations by IDE (see Table 4). Overall, 33 (8.40%) clinical samples were tested positive by ALK, ROS1, RET IDE. The IDE assay has a failed rate of 3.67%.

TABLE 4

ALK, ROS1, RET prevalence by IDE.

| IDE Result | # (%) |
|---|---|
| All Negative (ALK, ROS1, RET) | 360 (91.6) |
| ALK Positive | 20 (5.09) |
| ROS1 Positive | 3 (0.76) |
| RET Positive | 10 (2.54) |
| QNS | 15 (3.67) |
| Total | 408 |

For ALK, 20 of the samples were tested positive by IDE (Table 5). 15/20 samples were known ALK positive by FISH and/or EML4-ALK. 5/20 samples were tested positive by IDE but negative by FISH or EML4-ALK (false positive). In addition, one FISH positive sample was tested negative by both IDE and EML4-ALK (false negative).

TABLE 5

ALK IDE result summary.

|  |  | ALK FISH and/or EML4-ALK | |
|---|---|---|---|
|  |  | POS | NEG |
| ALK IDE | POS | 15 | 5 |
| ALK IDE | NEG | 1 | 372 |

For ROS1, both ROS1-positive cell lines and 3/408 (0.76%) NSCLC samples tested positive by IDE (Table 6). ROS1 and ALK IDE positivity were mutually exclusive. Among the 3 IDE-positive NSCLC samples, 1 was confirmed positive by FISH, and 1 was negative by FISH.

TABLE 6

ROS1 IDE result summary.

|  |  | ALK Results | |
|---|---|---|---|
|  |  | POS | NEG |
| ROS1 IDE | POS | 0 | 3 |
| ROS1 IDE | NEG | 21 | 369 |

|  |  | ROS1 FISH | |
|---|---|---|---|
|  |  | POS | NEG |
| ROS1 IDE | POS | 1 | 1 |
| ROS1 IDE | NEG | 0 | 6 |

For RET, all 7 known RET positives and 10/408 (2.5%) NSCLC samples tested positive by IDE (Table 7). RET and ALK IDE positivity were mutually exclusive. Among the 10 IDE-positive clinical samples, 4 were confirmed positive by FISH or RET-PTC, and 2 were negative by FISH.

TABLE 7

RET IDE result summary.

|  |  | ALK Results | |
|---|---|---|---|
|  |  | POS | NEG |
| RET IDE | POS | 0 | 10 |
| RET IDE | NEG | 21 | 362 |

|  |  | RET FISH | |
|---|---|---|---|
|  |  | POS | NEG |
| RET IDE | POS | 4 | 2 |
| RET IDE | NEG | 0 | 2 |

ALK IDE Assay Characteristics:

ALK IDE true positive clinical samples (with confirmed positive results by FISH and/or EML4-ALK) displayed higher ΔCt (average 6.87), compared to that of ALK IDE true negative samples (ΔCt average at 2.11, Table 8). ALK IDE false positive samples (with negative results by FISH and/or EML4-ALK) displayed a ΔCt range in between.

TABLE 8

ALK IDE ΔCt range for clinical samples.

| ALK IDE | # samples | ΔCt range | Average |
|---|---|---|---|
| True Positive | 15 | 4.4~10.7 | 6.87 |
| False Positive | 5 | 4.0~7.8 | 6.26 |
| True Negative | 372 | (1.2)~3.9 | 2.11 |

Results from the concordance study among ALK FISH, EML4-ALK, and ALK IDE indicated a 96.9% (186/192) concordance between IDE and FISH and 96.4% (185/192) concordance between IDE and EML4-ALK (Table 9). 3 EML4-ALK negative samples were positive by both FISH and IDE, while 1 ALK FISH negative sample was positive by both EML4-ALK and IDE. There were 1 false negative (FISH positive, but negative by both IDE and EML4-ALK) and 4 false positives (IDE positive, but FISH and EML4-ALK negative) samples.

TABLE 9

ALK concordance study: FISH vs EML4-ALK, vs IDE.

| # samples | ATX FISH | EML4-ALK | ATX IDE |
|---|---|---|---|
| 12 | POS | POS | POS |
| 3 | POS | NEG | POS |
| 1 | NEG | POS | POS |
| 1 | POS | NEG | NEG |
| 4 | NEG | NEG | POS |
| 171 | NEG | NEG | NEG |

To calculate the sensitivity and specificity of ALK IDE assay, there were 15 true positive samples, 5 false positive samples (IDE positive, but FISH and/or EML4-ALK negative), 1 false negative (FISH positive, but IDE and EML4-ALK negative), and 372 true negative samples (see Table 5).

Thus, the assay performance characteristics for ALK IDE were calculated as follows:

Sensitivity=TP/(TP+FN)*100%=93.7%

Specificity=TN/(FP+TN)*100%=98.7%

Positive Predictive Value (PPV)= TP/(TP+FP)*100%=75%

Negative Predictive Value (NPV)= TN/(TN+FN)*100%=99.7%

In summary, a total of 416 samples (408 lung cancer clinical samples and 2 ROS1 positive cell lines, and 7 RET positive clinical samples) were used to establish assay performance characteristics for IDE. All except one known ALK, ROS1, and RET translocation positive samples were correctly identified by IDE. The translocation positivity rate for IDE was 5.09% for ALK, 0.76% for ROS1, and 2.54% for RET.

The ALK, ROS1, RET IDE assays may be used as either stand-alone tests, or be employed as an effective screening tool to pick up putative translocation positive samples for confirmation by FISH or other follow-up method. In addition, additional translocation/rearrangement markers for NSCLC patients (ex. NTRK, BRAF, etc.) or additional disease-oriented translocation panels (ex. Thyroid) may be examined using the same IDE strategy.

OTHER EMBODIMENTS

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

REFERENCES

1. Howlader N et al. *SEER Cancer Statistics Review*, 1975-2009 (2012) National Cancer Institute. Bethesda, Md.,
2. Herbst R S and Bunn P A Jr. Targeting the epidermal growth factor receptor in non-small cell lung cancer. *Clin Cancer Res.* (2003) 9:5813-24.
3. Soda M et al. Identification of the transforming EML4-ALK fusion gene in non-small-cell lung cancer. *Nature* (2007) 448:561-6.
4. Howlader N et al. *SEER Cancer Statistics Review*, 1975-2009 (2012) Rikova K et al. Global survey of phosphotyrosine signaling identifies oncogenic kinases in lung cancer. *Cell* (2007) 131:1190-203.
5. Takeuchi K et al. KIF5B-ALK, a novel fusion oncokinase identified by an immunohistochemistry-based diagnostic system for ALK-positive lung cancer. *Clin Cancer Res.* (2009) 15:3143-9.
6. Kwak E L et al. Anaplastic lymphoma kinase inhibition in non-small-cell lung cancer. *N Engl J Med.* (2010) 363: 1693-703.
7. Takeuchi K et al. RET, ROS1 and ALK fusions in lung cancer. *Nat Med.* (2012) 18:378-81.
8. Rimkunas V M et al. Analysis of receptor tyrosine kinase ROS1-positive tumors in non-small cell lung cancer: identification of a FIG-ROS1 fusion. *Clin Cancer Res.* (2012) 18:4449-57.
9. Suehara Y et al. Identification of KIF5B-RET and GOPC-ROS1 Fusions in Lung Adenocarcinomas through a Comprehensive mRNA-Based Screen for Tyrosine Kinase Fusions. *Clin Cancer Res.* (2012) 18:6599-608.
10. Bergethon K et al. ROS1 rearrangements define a unique molecular class of lung cancers. *J Clin Oncol.* (2012) 30:863-70.
11. Kohno T et al. KIF5B-RET fusions in lung adenocarcinoma. *Nat Med.* (2012) 18:375-7.
12. Sanders, H R, Li H R, Bruey J M, Scheerle J A, Meloni-Ehrig A M, Kelly J C, Novick C, Albitar M. Exon scanning by reverse transcriptase-polymerase chain reaction for detection of known and novel EML4-ALK fusion variants in non-small cell lung cancer. Cancer Genet. 2011 204:45-52.
13. Cyniak-Magierska A, Wojciechowska-Durczyńska K, Krawczyk-Rusiecka K, Zygmunt A, Lewiński A. Assessment of RET/PTC1 and RET/PTC3 rearrangements in fine-needle aspiration biopsy specimens collected from patients with Hashimoto's thyroiditis. *Thyroid Res.* (2011) 4:5.

---

What is claimed is:

1. A composition comprising:
  (a) two or more 5' target primer pairs that are complementary to a 5' region of a ALK target gene transcript and are suitable for amplifying a 5' region of the target gene transcript, wherein at least one primer of each of the ALK 5' target primer pairs is detectably labeled; and
  (b) two or more 3' target primer pairs that are complementary to the 3' region of the ALK target gene transcript and are suitable for amplifying a 3' region of the target gene transcript, wherein at least one primer of each of the ALK 3' target primer pairs is detectably labeled;

and/or
  (c) two or more 5' target primer pairs that are complementary to a 5' region of a ROS1 target gene transcript and are suitable for amplifying a 5' region of the target gene transcript, wherein at least one primer of each of the ROS1 5' target primer pairs is detectably labeled; and
  (d) two or more 3' target primer pairs that are complementary to the 3' region of the ROS1 target gene transcript and are suitable for amplifying a 3' region of the target gene transcript, wherein at least one primer of each of the ROS1 3' target primer pairs is detectably labeled;

and/or
  (e) two or more 5' target primer pairs that are complementary to a 5' region of a RET target gene transcript and are suitable for amplifying a 5' region of the target gene transcript, wherein at least one primer of each of the RET 5' target primer pairs is detectably labeled; and
  (f) two or more 3' target primer pairs that are complementary to the 3' region of the RET target gene transcript and are suitable for amplifying a 3' region of the target gene transcript, wherein at least one primer of each of the RET 3' target primer pairs is detectably labeled; and
  (g) a biological sample.

2. The composition of claim 1, further comprising one or more reagents for performing a nucleic acid amplification reaction.

3. The composition of claim 1, wherein the two or more ALK 5' target primer pairs comprises a primer pair having:
  a forward primer of SEQ ID NO: 1 and a reverse primer of SEQ ID NO: 2;
  a forward primer of SEQ ID NO: 3 and a reverse primer of SEQ ID NO: 4;
  a forward primer of SEQ ID NO: 5 and a reverse primer of SEQ ID NO: 6;
  a forward primer of SEQ ID NO: 7 and a reverse primer of SEQ ID NO: 8; and/or a forward primer of SEQ ID NO: 9 and a reverse primer of SEQ ID NO: 10.

4. The composition of claim 1, wherein the two or more ALK 3' target primer pairs comprises a primer pair having:
a forward primer of SEQ ID NO: 11 and a reverse primer of SEQ ID NO: 12;
a forward primer of SEQ ID NO: 13 and a reverse primer of SEQ ID NO: 14;
a forward primer of SEQ ID NO: 15 and a reverse primer of SEQ ID NO: 16;
a forward primer of SEQ ID NO: 17 and a reverse primer of SEQ ID NO: 18; and/or
a forward primer of SEQ ID NO: 19 and a reverse primer of SEQ ID NO: 20.

5. The composition of claim 1, wherein the two or more ROS1 5' target primer pairs comprises a primer pair having:
a forward primer of SEQ ID NO: 21 and a reverse primer of SEQ ID NO: 22;
a forward primer of SEQ ID NO: 23 and a reverse primer of SEQ ID NO: 24;
a forward primer of SEQ ID NO: 25 and a reverse primer of SEQ ID NO: 26;
a forward primer of SEQ ID NO: 27 and a reverse primer of SEQ ID NO: 28; and/or
a forward primer of SEQ ID NO: 29 and a reverse primer of SEQ ID NO: 30.

6. The composition of claim 1, wherein the two or more ROS1 3' target primer pairs comprises a primer pair having:
a forward primer of SEQ ID NO: 31 and a reverse primer of SEQ ID NO: 32;
a forward primer of SEQ ID NO: 33 and a reverse primer of SEQ ID NO: 34;
a forward primer of SEQ ID NO: 35 and a reverse primer of SEQ ID NO: 36;
a forward primer of SEQ ID NO: 37 and a reverse primer of SEQ ID NO: 38; and/or
a forward primer of SEQ ID NO: 39 and a reverse primer of SEQ ID NO: 40.

7. The composition of claim 1, wherein the two or more RET 5' target primer pairs comprises a primer pair having:
a forward primer of SEQ ID NO: 41 and a reverse primer of SEQ ID NO: 42;
a forward primer of SEQ ID NO: 43 and a reverse primer of SEQ ID NO: 44;
a forward primer of SEQ ID NO: 45 and a reverse primer of SEQ ID NO: 46;
a forward primer of SEQ ID NO: 47 and a reverse primer of SEQ ID NO: 48; and/or
a forward primer of SEQ ID NO: 49 and a reverse primer of SEQ ID NO: 50.

8. The composition of claim 1, wherein the two or more RET 3' target primer pairs comprises a primer pair having:
a forward primer of SEQ ID NO: 51 and a reverse primer of SEQ ID NO: 52;
a forward primer of SEQ ID NO: 53 and a reverse primer of SEQ ID NO: 54;
a forward primer of SEQ ID NO: 55 and a reverse primer of SEQ ID NO: 56;
a forward primer of SEQ ID NO: 57 and a reverse primer of SEQ ID NO: 58; and/or
a forward primer of SEQ ID NO: 59 and a reverse primer of SEQ ID NO: 60.

9. The composition of claim 1, further comprising an oligonucleotide probe that is complementary to an amplification product generated by amplification with a ALK 5' target primer pair of (a) and/or an oligonucleotide probe that is complementary to an amplification product generated by amplification with a ALK 3' target primer pair of (b).

10. The composition of claim 1, further comprising an oligonucleotide probe that is complementary to an amplification product generated by amplification with a ROS1 5' target primer pair of (c) and/or an oligonucleotide probe that is complementary to an amplification product generated by amplification with a ROS1 3' target primer pair of (d).

11. The composition of claim 1, further comprising an oligonucleotide probe that is complementary to an amplification product generated by amplification with a RET 5' target primer pair of (e) and/or an oligonucleotide probe that is complementary to an amplification product generated by amplification with a RET 3' target primer pair of (f).

12. The composition of claim 2, wherein the nucleic acid amplification reaction is a quantitative real-time polymerase chain reaction (PCR).

13. The composition of claim 1, wherein the biological sample is obtained from a human subject.

14. The composition of claim 1, wherein the biological sample is selected from the group consisting of whole blood, isolated blood cells, plasma, serum, tissue, fresh frozen tissue, formulain-fixed paraffin-embedded tissue, and urine.

15. A method for detecting a dysregulation in an ALK gene comprising:
(a) amplifying portions of a 5' region of a transcript of the ALK gene or a cDNA derived therefrom, if present in a test sample, with two or more different 5' target primer pairs comprising a primer pair having:
a forward primer of SEQ ID NO: 1 and a reverse primer of SEQ ID NO: 2;
a forward primer of SEQ ID NO: 3 and a reverse primer of SEQ ID NO: 4;
a forward primer of SEQ ID NO: 5 and a reverse primer of SEQ ID NO: 6;
a forward primer of SEQ ID NO: 7 and a reverse primer of SEQ ID NO: 8; and/or
a forward primer of SEQ ID NO: 9 and a reverse primer of SEQ ID NO: 10;
(b) amplifying portions of a 3' region of the transcript of the ALK gene or a cDNA derived therefrom, if present in the test sample, with two or more different 3' target primer pairs that are directed to the portions of the 3' region of the ALK gene;
(c) detecting the amplification products produced by the two or more 5' target primer pairs and the two or more 3' target primer pairs;
(d) determining the average cycle threshold (Ct) among the two or more 5' target primer pairs and the average Ct among the two or more 3' target primer pairs; and
(e) identifying the nucleic acid sample as having a gene dysregulation when the average Ct among the two or more 5' target primer pairs and the average Ct among the two or more 3' target primer pairs as determined in step (d) indicate that the ALK gene is dysregulated.

16. The method of claim 15, wherein the two or more ALK 3' target primer pairs comprises a primer pair having:
a forward primer of SEQ ID NO: 11 and a reverse primer of SEQ ID NO: 12;
a forward primer of SEQ ID NO: 13 and a reverse primer of SEQ ID NO: 14;
a forward primer of SEQ ID NO: 15 and a reverse primer of SEQ ID NO: 16;
a forward primer of SEQ ID NO: 17 and a reverse primer of SEQ ID NO: 18; and/or
a forward primer of SEQ ID NO: 19 and a reverse primer of SEQ ID NO: 20.

17. The method of claim 15, wherein the detecting is accomplished using an oligonucleotide probe that is complementary to an amplification product generated by amplification with a ALK 5' target primer pair of (a) and/or an oligonucleotide probe that is complementary to an amplification product generated by amplification with a ALK 3' target primer pair of (b).

18. The method of claim 15, wherein at least one primer in each of the two or more 5' target primer pairs comprises a first detectable label and at least one primer in each of the two or more 3' target primer pairs comprises a second detectable label.

19. The method of claim 15, wherein the amplifying is performed using quantitative real-time polymerase chain reaction (PCR).

20. A method for detecting a dysregulation in an ROS1 gene comprising:
(a) amplifying portions of a 5' region of a transcript of the ROS1 gene or a cDNA derived therefrom, if present in a test sample, with two or more different 5' target primer pairs comprising a primer pair having:
a forward primer of SEQ ID NO: 21 and a reverse primer of SEQ ID NO: 22;
a forward primer of SEQ ID NO: 23 and a reverse primer of SEQ ID NO: 24;
a forward primer of SEQ ID NO: 25 and a reverse primer of SEQ ID NO: 26;
a forward primer of SEQ ID NO: 27 and a reverse primer of SEQ ID NO: 28; and/or
a forward primer of SEQ ID NO: 29 and a reverse primer of SEQ ID NO: 30;
(b) amplifying portions of a 3' region of the transcript of the ROS1 gene or a cDNA derived therefrom, if present in the test sample, with two or more different 3' target primer pairs that are directed to the portions of the 3' region of the ROS1 gene;
(c) detecting the amplification products produced by the two or more 5' target primer pairs and the two or more 3' target primer pairs;
(d) determining the average cycle threshold (Ct) among the two or more 5' target primer pairs and the average Ct among the two or more 3' target primer pairs; and
(e) identifying the nucleic acid sample as having a gene dysregulation when the average Ct among the two or more 5' target primer pairs and the average Ct among the two or more 3' target primer pairs as determined in step (d) indicate that the ROS1 gene is dysregulated.

21. The method of claim 20, wherein the two or more ROS1 3' target primer pairs comprises a primer pair having:
a forward primer of SEQ ID NO: 31 and a reverse primer of SEQ ID NO: 32;
a forward primer of SEQ ID NO: 33 and a reverse primer of SEQ ID NO: 34;
a forward primer of SEQ ID NO: 35 and a reverse primer of SEQ ID NO: 36;
a forward primer of SEQ ID NO: 37 and a reverse primer of SEQ ID NO: 38; and/or
a forward primer of SEQ ID NO: 39 and a reverse primer of SEQ ID NO: 40.

22. The method of claim 20, wherein the detecting of (c) is accomplished using an oligonucleotide probe that is complementary to an amplification product generated by amplification with a ROS1 5' target primer pair of (a) and/or an oligonucleotide probe that is complementary to an amplification product generated by amplification with a ROS1 3' target primer pair of (b).

23. The method of claim 20, wherein at least one primer in each of the two or more 5' target primer pairs comprises a first detectable label and at least one primer in each of the two or more 3' target primer pairs comprises a second detectable label.

24. The method of claim 20, wherein the amplifying is performed using quantitative real-time polymerase chain reaction (PCR).

25. A method for detecting a dysregulation in an RET gene comprising:
(a) amplifying portions of a 5' region of a transcript of the RET gene or a cDNA derived therefrom, if present in a test sample, with two or more different 5' target primer pairs comprising a primer pair having:
a forward primer of SEQ ID NO: 41 and a reverse primer of SEQ ID NO: 42;
a forward primer of SEQ ID NO: 43 and a reverse primer of SEQ ID NO: 44;
a forward primer of SEQ ID NO: 45 and a reverse primer of SEQ ID NO: 46;
a forward primer of SEQ ID NO: 47 and a reverse primer of SEQ ID NO: 48; and/or
a forward primer of SEQ ID NO: 49 and a reverse primer of SEQ ID NO: 50;
(b) amplifying portions of a 3' region of the transcript of the RET gene or a cDNA derived therefrom, if present in the test sample, with two or more different 3' target primer pairs that are directed to the portions of the 3' region of the RET gene;
(c) detecting the amplification products produced by the two or more 5' target primer pairs and the two or more 3' target primer pairs;
(d) determining the average cycle threshold (Ct) among the two or more 5' target primer pairs and the average Ct among the two or more 3' target primer pairs; and
(e) identifying the nucleic acid sample as having a gene dysregulation when the average Ct among the two or more 5' target primer pairs and the average Ct among the two or more 3' target primer pairs as determined in step (d) indicate that the RET gene is dysregulated.

26. The method of claim 25, wherein the two or more RET 3' target primer pairs comprises a primer pair having:
a forward primer of SEQ ID NO: 51 and a reverse primer of SEQ ID NO: 52;
a forward primer of SEQ ID NO: 53 and a reverse primer of SEQ ID NO: 54;
a forward primer of SEQ ID NO: 55 and a reverse primer of SEQ ID NO: 56;
a forward primer of SEQ ID NO: 57 and a reverse primer of SEQ ID NO: 58; and/or
a forward primer of SEQ ID NO: 59 and a reverse primer of SEQ ID NO: 60.

27. The method of claim 25, the detecting of (c) is accomplished with an oligonucleotide probe that is complementary to an amplification product generated by amplification with a RET 5' target primer pair of (a) and/or an oligonucleotide probe that is complementary to an amplification product generated by amplification with a RET 3' target primer pair of (b).

28. The method of claim 25, wherein at least one primer in each of the two or more 5' target primer pairs comprises a first detectable label and at least one primer in each of the two or more 3' target primer pairs comprises a second detectable label.

29. The method of claim 25, wherein the amplifying is performed using quantitative real-time polymerase chain reaction (PCR).

* * * * *

SEQUENCE LISTING

```
<160> NUMBER OF SEQ ID NOS: 66

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gatggacttg ctggatggg                                                  19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 2
atggtgtgct tggagtcag        19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atctgcttct gtgaccacg        19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agaggatcag cgagagtgg        19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccctgaaagg catccagatc        20

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcatggtgtt cttcccgc        18

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catcagcctg gactgctacc t        21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtgctgtat tctgcaggat ctt                                           23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 9
cttccctttc ctgtctcatc g                                             21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 10
ttcctgaggt catgcagtg                                                19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 11
tgtggctgtc agtatttgga g                                             21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 12
aggtcaagag gcagtttctg                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 13
caagacctcc tccatcagtg                                               20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 14
ccttcataca cctccccaaa g                                               21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaatgcccaa cgacccaag                                                  19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tccatgagga aatccagttc g                                               21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaagacaggc ccaactttgc                                                 20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgggtcctgg gtgcagtat                                                  19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtgtatgaag gccaggtgtc                                                 20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctggtggttg aatttgctga tg                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
actccctcag tgatgtctttt tc                                             22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cctggcccct tagatgtaaa g                                               21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caggctcttg ttcaatggaa g                                               21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcagaagggc ctaattcaaa g                                               21

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctcatcagat tttgggttga gcta                                            24

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gctgcatgaa gttttaacat ggtaa                                           25

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
cagtcaatgt attcacctgt aca                                    23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tttcagaagt actccaggct g                                      21

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
cacttttgga actctgtaga tcag                                   24

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
cctcttcata tgcaccttcc g                                      21

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
aacagtggag tcataaatga aagc                                   24

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ttcgtttcca ttaaagcaac tgg                                    23

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctatgtgcaa acaggaggga                                             20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tctttggtcg ggttcttgag                                             20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgtgtctact tggaacggat g                                           21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tcactatccg tggactggta ta                                          22

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cagcagtgga catcttagga gttg                                        24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggaacccttc ttcaaagtct tcac                                        24

<210> SEQ ID NO 39

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tggacatctt aggagttgga agtg                                          24

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggtctgtgga acccttcttc aa                                            22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttgtggagac ccaagacatc                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccatagccag ctttaatccc                                               20

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgtctgctgt tgctgctg                                                 18

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctggtccaca tacagcttct                                               20

<210> SEQ ID NO 45
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agcagacctc taggcagg                                                      18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gccgtctctt gctgactg                                                      18

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgccgctgct aggcaaa                                                       17

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccagtaagca tccctcgaga a                                                  21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aaggagatgg caaagggatc                                                    20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
atgttgatgt cttgggtctc c                                                  21

<210> SEQ ID NO 51
<211> LENGTH: 21
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 51
agggtcggat tccagttaaa t                                              21

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
cctagggtca cgatctcc                                                  18

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
gtcccgagat gtttatgaag ag                                             22

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
tgcgtggtgt agatatgatc aaa                                            23

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
ggatgcagta tctggccg                                                  18

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ctcagctacc aggatgtttc                                                20

<210> SEQ ID NO 57
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 57
cccacatgtc atcaaattgt atgg                                              24

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttggcgtact ccacgatgag                                                   20

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gaaacatcct ggtagctgag g                                                 21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tttaactgga atccgaccct g                                                 21

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcatgttggc agtggaatc                                                    19

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgtctgagat actggattcc tg                                                22

<210> SEQ ID NO 63
<211> LENGTH: 23
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 63
tcctccagct gttatctgga aga                                              23

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tgggtccagc gagaaggtt                                                   19

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gtcctcgtcc tccagctgtt a                                                21

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gaggctcaaa gtcagatgct actg                                             24
```